US009679452B2

(12) United States Patent
Joo et al.

(10) Patent No.: US 9,679,452 B2
(45) Date of Patent: Jun. 13, 2017

(54) SOUND FIELD SECURITY SYSTEM AND METHOD OF DETERMINING STARTING POINT FOR ANALYSIS OF RECEIVED WAVEFORM USING THE SAME

(71) Applicants: MCNEX CO., LTD., Seoul (KR); EYECLON INC., Irvine, CA (US); MCNEX (Shanghai) Electronics Co., Ltd., Shanghai (CN)

(72) Inventors: Sung Il Joo, Seoul (KR); Hun Kang, Seoul (KR)

(73) Assignees: MCNEX Co., Ltd., Seoul (KR); Eyeclon Inc., Irvine, CA (US); MCNEX (Shanghai) Electronics Co., Ltd., Shanghai (CN)

( * ) Notice: Subject to any disclaimer, the term of this patent is extended or adjusted under 35 U.S.C. 154(b) by 0 days.

(21) Appl. No.: 15/017,736

(22) Filed: Feb. 8, 2016

(65) Prior Publication Data

US 2016/0241977 A1 Aug. 18, 2016

(30) Foreign Application Priority Data

Feb. 12, 2015 (KR) ........................ 10-2015-0021791

(51) Int. Cl.

| | |
|---|---|
| ***H04R 29/00*** | (2006.01) |
| ***A61F 11/06*** | (2006.01) |
| ***G10K 11/16*** | (2006.01) |
| ***H03B 29/00*** | (2006.01) |
| ***G08B 13/16*** | (2006.01) |
| *H04R 3/00* | (2006.01) |

(52) U.S. Cl.
CPC ............ *G08B 13/1609* (2013.01); *H04R 3/00* (2013.01)

(58) Field of Classification Search
CPC ......... H04R 29/00; H04R 1/02; H04R 29/007
USPC ............................. 381/56, 71.8, 58, 59, 71.4
See application file for complete search history.

(56) References Cited

U.S. PATENT DOCUMENTS

| | | | | |
|---|---|---|---|---|
| 7,869,611 | B2 * | 1/2011 | Asada | H04S 7/301 381/122 |
| 8,546,674 | B2 * | 10/2013 | Kurihara | H04R 29/008 84/464 R |
| 8,797,407 | B2 | 8/2014 | Lee et al. | |
| 9,197,976 | B2 | 11/2015 | Park et al. | |
| 2012/0087211 | A1 | 4/2012 | Lee et al. | |

(Continued)

FOREIGN PATENT DOCUMENTS

| | | |
|---|---|---|
| KR | 10-2011-0067243 A | 6/2011 |
| KR | 10-2012-0037855 A | 4/2012 |

(Continued)

OTHER PUBLICATIONS

Korean Notice of Allowance issued in counterpart Korean Application No. 10-2015-0021791 (2 pages in Korean).

*Primary Examiner* — Thjuan K Addy
(74) *Attorney, Agent, or Firm* — NSIP Law

(57) ABSTRACT

Provided is a sound field security system with improved sound field analysis performance, and a method of determining a starting point for analysis of a received waveform by using the same, in which a starting point for analysis of a received waveform may be accurately determined even when there are irregular delays in a system, thereby enabling sound field analysis to be more adaptive to irregular delays that may occur in the system, and ensuring stable sound field security.

10 Claims, 4 Drawing Sheets

(56) References Cited

U.S. PATENT DOCUMENTS

| | | | | |
|---|---|---|---|---|
| 2013/0162821 | A1 * | 6/2013 | Park | G08B 13/19695 348/143 |
| 2014/0307096 | A1 | 10/2014 | Park et al. | |

FOREIGN PATENT DOCUMENTS

| | | | |
|---|---|---|---|
| KR | 10-2013-0074437 | A | 7/2013 |
| KR | 10-2014-0124317 | A | 10/2014 |

* cited by examiner

SOUND FIELD SECURITY SYSTEM AND METHOD OF DETERMINING STARTING POINT FOR ANALYSIS OF RECEIVED WAVEFORM USING THE SAME

CROSS-REFERENCE TO RELATED APPLICATION(S)

This application claims priority from Korean Patent Application No. 10-2015-0021791, filed on Feb. 12, 2015, in the Korean Intellectual Property Office, the entire disclosure of which is incorporated herein by reference for all purposes.

BACKGROUND

1. Field

The following description generally relates to sound field security, and more particularly to a sound field security system and a method of determining a starting point for analysis of a received waveform.

2. Description of the Related Art

Korean Laid-open Patent Publication No. 10-2013-0074437 (Jul. 4, 2013) discloses a sound field security system that determines intrusion by analyzing variations in a sound field pattern. Such existing sound field security system analyzes data stored during a specific period of time, so as to determine intrusion by analyzing a temporal relationship of sound pressures.

A sound output unit, which outputs a sound signal, and a sound receiver, which receives the sound signal output from the sound output unit, are spaced apart from each other, such that the sound receiver receives the sound signal output from the sound output unit at a delayed time.

However, if such time delay occurs regularly, a waveform may be analyzed from a point in time (temporal location) after a regular delay, but a system delay may not guarantee that such delay is regular.

Accordingly, the inventors of the present disclosure conducted research on a sound field security system with improved sound field analysis performance, which may be adaptive to irregular delays occurring in a system, so that more accurate and stable sound field security may be ensured.

SUMMARY

Provided is a sound field security system with improved sound field analysis performance, which may be adaptive to irregular delays occurring in a system, and a method of determining a starting point for analysis of a received waveform by using the same.

In one general aspect, there is provided a sound field security system with improved sound field analysis performance, the system including: a sound output unit configured to output a sound signal; a sound receiver configured to receive the sound signal output by the sound output unit; and a sound analyzer configured to analyze a temporal relationship of sound pressures of the sound signal received by the sound receiver, so as to determine intrusion, wherein the sound analyzer may include: a combined value calculator configured to calculate combined values by combining received waveform amplitudes at locations, corresponding to locations in intervals of peaks of an output waveform of the sound signal output by the sound output unit, at each time-axis location of the received waveform of the sound signal received by the sound receiver; a location selector configured to select a time-axis location of the received waveform, the time-axis location having a maximum combined value, from among the combined values, calculated by the combined value calculator at each time-axis location of the received waveform of the sound signal; and a starting point determiner configured to determine, as a starting point for analysis of the received waveform, a time-axis location obtained by deducting a specific time set value from the selected time-axis location of the received waveform.

The specific time set value deducted from the selected time-axis location of the received waveform may be an interval between a temporal location of a first peak of the output waveform and a starting point of the output waveform.

The sound signal, output by the sound output unit, may include a continuously repeated sound period having at least two output waveform peaks.

Each of the sound periods may include silent periods during the specific time set value before the starting point of the output waveform.

Each of the sound periods may include silent periods during the specific time set value after an end point of the output waveform.

The intervals of peaks of the output waveform may be regular.

The intervals of peaks of the output waveform may be irregular.

In another general aspect, there is provided a method of determining a starting point for analysis of a received waveform of a sound field security system, the method including: calculating combined values by combining received waveform amplitudes at locations, corresponding to locations in intervals of peaks of the output waveform of a sound signal, at each time-axis location of the received waveform of the sound signal; selecting a time-axis location of the received waveform, the time-axis location having a maximum combined value, from among the combined values obtained by the calculation at each time-axis location of the received waveform of the sound signal; and determining, as a starting point for analysis of the received waveform, a time-axis location obtained by deducting a specific time set value from the selected time-axis location of the received waveform.

Figure 1:
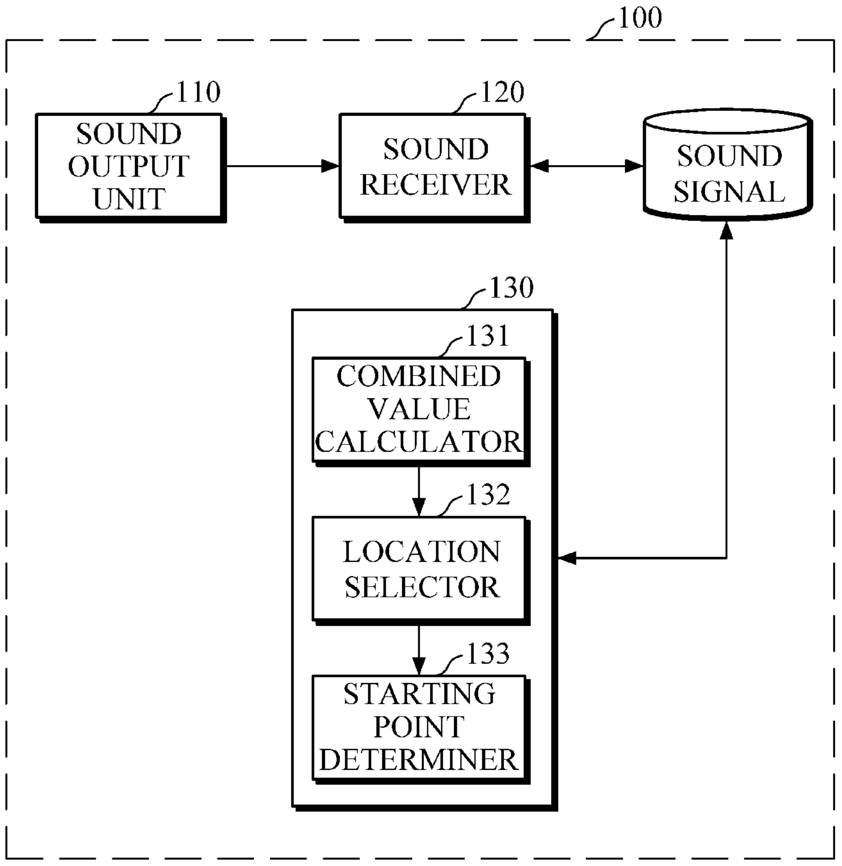
FIG. 1 is a block diagram illustrating an example of a sound field security system with improved sound field analysis performance according to an exemplary embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Hereinafter, exemplary embodiments of the present disclosure will be described with reference to the accompanying drawings.

In the following description, a detailed description of known functions and configurations incorporated herein will be omitted when it may obscure the subject matter of the present invention.

Further, the terms used throughout this specification are defined in consideration of the functions according to exemplary embodiments, and can be varied according to a purpose of a user or manager, or precedent and so on. Therefore, definitions of the terms should be made on the basis of the overall context.

FIG. 1 is a block diagram illustrating an example of a sound field security system with improved sound field analysis performance according to an exemplary embodiment. As illustrated in FIG. 1, the sound field security system 100 with improved sound field analysis performance includes a sound output unit 110, a sound receiver 120, and a sound analyzer 130.

The sound output unit 110 outputs a sound signal, in which the sound signal, output by the sound output unit 110, may be configured to include a continuously repeated sound period having at least two output waveform peaks. In this case, intervals between the output waveform peaks may be regular or irregular.

Each sound period may be configured to include a silent period during a specific time set value before a starting point of the output waveform. Further, each sound period may be configured to include a silent period during a specific time set value after an end point of the output waveform.

Figure 2:
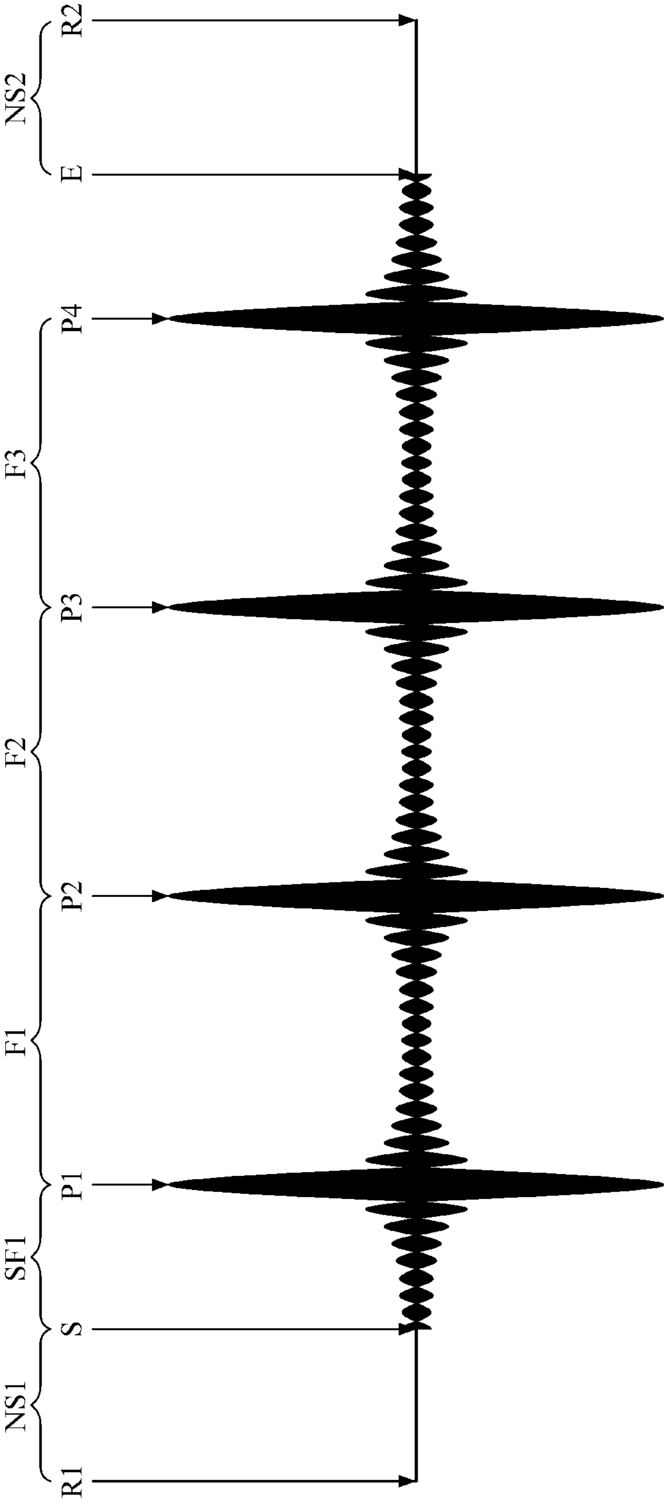
FIG. 2 is a waveform diagram illustrating an example of an output waveform of a sound signal output by a sound output unit of the sound field security system with improved sound field analysis performance according to an exemplary embodiment.

FIG. 2 is a waveform diagram illustrating an example of an output waveform of a sound signal output by a sound output unit of the sound field security system with improved sound field analysis performance according to an exemplary embodiment, in which FIG. 2 illustrates an output waveform having four peaks in one sound period.

In FIG. 2, P1, P2, P3, and P4 indicate temporal locations of output waveform peaks, in which S represents a starting point of the output waveform, E represents an end point of the output waveform, and F1, F2, and F3 represents intervals between the temporal locations of the peaks, with F1=P2−P1, F2=P3−P2, and F3=P4−P3.

The SF1 represents an interval between a temporal location of the first peak and a temporal location of the starting point of the output waveform, in which SF1=P1−S. R1 represents a starting point of the sound period, R2 represents an end point of the sound period, and NS1 and NS2 are silent periods.

In this case, P1, P2, P3, P4, S, F1, F2, F3, SF1, NS1, and NS2 are predetermined values, which are determined depending on how characteristics of the output waveform of the sound signal output by the sound output unit are set.

Figure 3:
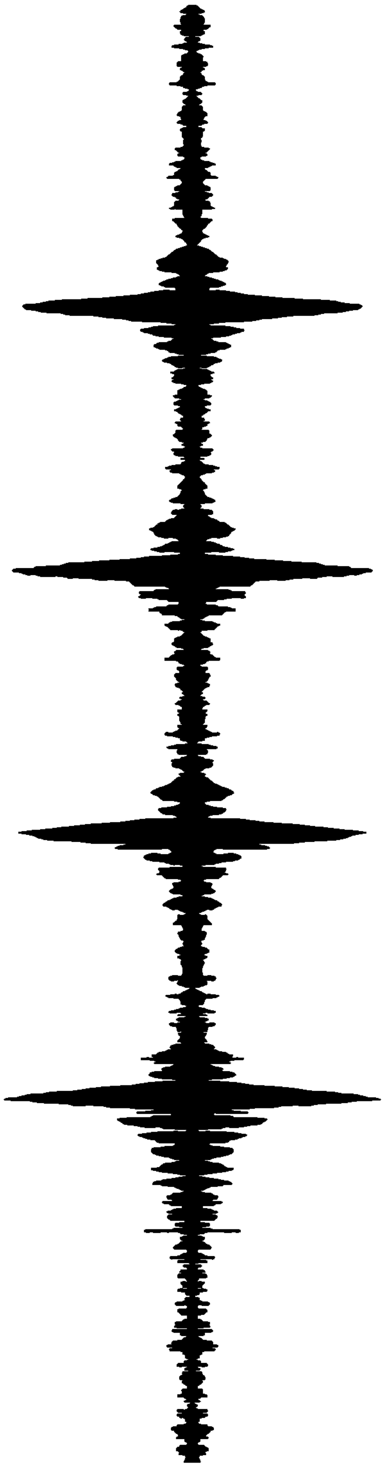
FIG. 3 is a waveform diagram illustrating an example of a received waveform of a sound signal received by a sound receiver of the sound field security system with improved sound field analysis performance according to an exemplary embodiment.

The sound receiver 120 receives a sound signal output by the sound output unit 110. FIG. 3 is a waveform diagram illustrating an example of a received waveform of a sound signal received by a sound receiver of the sound field security system with improved sound field analysis performance according to an exemplary embodiment, in which the received waveform in FIG. 3 is a waveform that is temporally delayed when compared to the output waveform illustrated in FIG. 2.

The sound output unit 110, which outputs a sound signal, and the sound receiver, which receives the sound signal output from the sound output unit 110, are spaced apart from each other, such that the sound receiver 120 receives the sound signal output from the sound output unit 110 at a delayed time.

However, if such time delay occurs regularly, a waveform may be analyzed from a point in time after a regular delay, but a system delay may not guarantee that such delay is regular.

The system delay may refer to a time delay caused by internal or external environments, such as equipment error, temperature change, vibrations, and the like. In order to ensure more precise and stable sound field security, the system is required to be adaptive to such irregular system delays.

The sound analyzer 130 may analyze a temporal relationship of sound pressures of a sound signal received by the sound receiver 120, to determine intrusion. In the present disclosure, the sound analyzer 130 includes a combined value calculator 131, a location selector 132, and a starting point determiner 133, so that a starting point for analysis of a received waveform may be accurately determined even when there are irregular delays in a system, thereby enabling sound field analysis to be more adaptive to irregular delays that may occur in the system, and ensuring stable sound field security.

The combined value calculator 131 calculates combined values obtained by combining received waveform amplitudes at locations, corresponding to locations in intervals of peaks of the output waveform of the sound signal output by the sound output unit 110, at each time-axis location of the received waveform of the sound signal received by the sound receiver 120.

Assuming that the time-axis location of the received waveform is i, values of received waveform amplitudes at locations, corresponding to locations in intervals of peaks of the output waveform, and a value obtained by combining the received waveform amplitudes may be represented as follows. For example, by increasing i to 1 sec. with the time interval of 0.1 sec., 10 values may be combined.

The received waveform amplitudes at i:

$$Sig_i, Sig_{i+F1}, Sig_{i+F1+F2}, Sig_{i+F1+F2+F3}$$

The combined value of the received waveform at i:

$$Sig_i, Sig_{i+F1}, Sig_{i+F1+F2}, Sig_{i+F1+F2+F3}$$

The location selector 132 selects a time-axis location mp of the received waveform, the time-axis location having a maximum combined value, from among the combined values, calculated by the combined value calculator 131 at each time-axis location of the received waveform of the sound signal.

That is, the intervals between peaks of the output waveform may be identical as long as the waveform is not transformed, and a location of a first peak of the received waveform may be a temporal location having a maximum combined value, among combined values obtained by combining received waveform amplitudes at locations corresponding to locations in intervals of peaks of the output waveform and calculated by increasing each temporal location of the received waveform.

The starting point location determiner 133 determines, as a starting point for analysis of the received waveform, a time-axis location obtained by deducting a specific time set value from the time-axis location of the received waveform that is selected by the location selector 132.

In this case, the specific time set value deducted from the time-axis location of the received waveform may be SF1=P1−S, which is an interval between a temporal location of the first peak of the output waveform and a starting point of the output waveform. Thus, the starting point for analysis of the received waveform that is determined by the starting point determiner 133 may be S'=mp−SF1.

Upon determining the starting point of the output waveform, the sound analyzer 130 analyzes a received waveform pattern of a sound period, i.e., a temporal relationship of sound pressures of a sound signal, so as to determine intrusion.

In this manner, a starting point for analysis of a received waveform may be accurately determined even when there are irregular delays in a system, thereby enabling sound field analysis to be more adaptive to irregular delays that may occur in the system, and ensuring stable sound field security.

Figure 4:
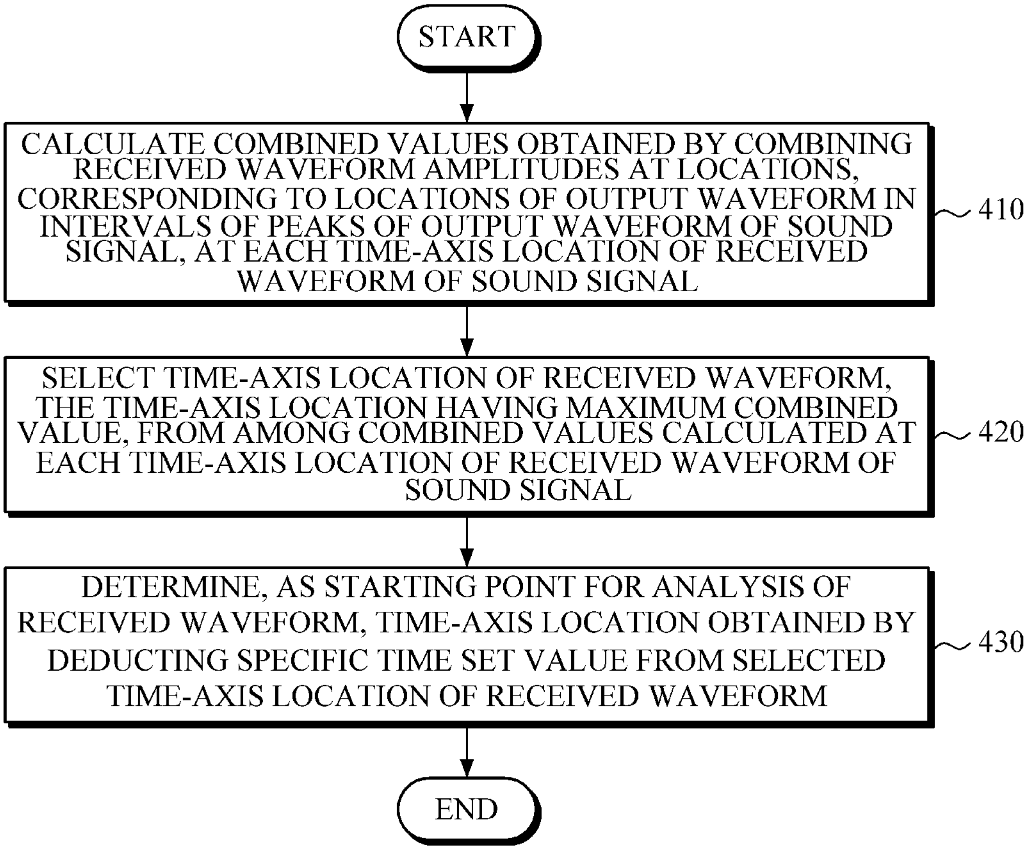
FIG. 4 is a flowchart illustrating a method of determining a starting point for analysis of the received waveform by using the sound field security system with improved sound field analysis performance according to an exemplary embodiment.

The sound field security system with improved sound field analysis performance performs a method of determining a starting point for analysis of a received waveform, which will be described with reference to FIG. 4. FIG. 4 is a flowchart illustrating a method of determining a starting point for analysis of the received waveform by using the sound field security system with improved sound field analysis performance according to an exemplary embodiment.

The sound field security system calculates combined values in 410 by combining received waveform amplitudes at locations, corresponding to locations in intervals of peaks of the output waveform of a sound signal, at each time-axis location of the received waveform of the sound signal. The calculation of combined values is described above, such that detailed descriptions thereof will be omitted.

Then, the sound field security system selects, in 420, a time-axis location of the received waveform, the time-axis location having a maximum combined value, from among the combined values obtained by the calculation at each time-axis location of the received waveform of the sound signal. The selection of the time axis location of the received waveform, which has a maximum combined value, is described above, such that detailed descriptions thereof will be omitted.

Subsequently in 430, the sound field security system determines, as a starting point for analysis of the received waveform, a time-axis location obtained by deducting a specific time set value from the time-axis location of the received waveform that is selected in 420 as the time-axis location having the maximum combined value. The determination of the starting point for analysis of the received waveform is described above, such that detailed descriptions thereof will be omitted.

As described above, a starting point for analysis of a received waveform may be accurately determined even when there are irregular delays in a system, thereby enabling sound field analysis to be more adaptive to irregular delays that may occur in the system, and ensuring stable sound field security.

The present disclosure may be used in applications related to sound field security.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims. Further, the above-described examples are for illustrative explanation of the present invention, and thus, the present invention is not limited thereto.

What is claimed is:

1. A sound field security system with improved sound field analysis performance, the system comprising:

a sound output unit configured to output a sound signal;

a sound receiver configured to receive the sound signal output by the sound output unit; and a sound analyzer configured to analyze a temporal relationship of sound pressures of the sound signal received by the sound receiver, so as to determine intrusion, wherein the sound analyzer comprises:

a combined value calculator configured to calculate combined values by combining received waveform amplitudes at locations, corresponding to locations in intervals of peaks of an output waveform of the sound signal output by the sound output unit, at each time-axis location of the received waveform of the sound signal received by the sound receiver;

a location selector configured to select a time-axis location of the received waveform, the time-axis location having a maximum combined value, from among the combined values, calculated by the combined value calculator at each time-axis location of the received waveform of the sound signal; and a starting point determiner configured to determine, as a starting point for analysis of the received waveform, a time-axis location obtained by deducting a specific time set value from the selected time-axis location of the received waveform.

2. The system of claim 1, wherein the specific time set value deducted from the selected time-axis location of the received waveform corresponds to an interval between a temporal location of a first peak of the output waveform and a starting point of the output waveform.

3. The system of claim 1, the sound signal, output by the sound output unit, includes a continuously repeated sound period having at least two output waveform peaks.

4. The system of claim 3, wherein each of the sound periods includes silent periods during the specific time set value before the starting point of the output waveform.

5. The system of claim 1, wherein each of the sound periods includes silent periods during the specific time set value after an end point of the output waveform.

6. The system of claim 3, wherein the intervals of peaks of the output waveform are regular.

7. The system of claim 3, wherein the intervals of peaks of the output waveform are irregular.

8. A method of determining a starting point for analysis of a received waveform of a sound field security system, the method comprising:

calculating combined values, by combining received waveform amplitudes at locations corresponding to locations in intervals of peaks of an output waveform of a sound signal, at each time-axis location of the received waveform of the sound signal;

selecting a time-axis location of the received waveform, the time-axis location having a maximum combined value, from among the combined values obtained by the calculation at each time-axis location of the received waveform of the sound signal; and determining, as a starting point for analysis of the received waveform, a time-axis location obtained by deducting a specific time set value from the selected time-axis location of the received waveform.

9. The method of claim 8, wherein the specific time set value deducted from the selected time-axis location of the received waveform corresponds to an interval between a temporal location of a first peak of the output waveform and a starting point of the output waveform.

10. The method of claim 8, wherein the specific time set value corresponds to a starting point of the received waveform, and the selected time-axis location of the received waveform corresponds to a first peak of the received waveform.

* * * * *